United States Patent [19]

Kablaoui et al.

[11] 4,013,697

[45] Mar. 22, 1977

[54] PREPARATION OF CARBOXYLIC ACIDS FROM SALTS OF NITROKETONES

[75] Inventors: Mahmoud S. Kablaoui, Wappingers Falls; Richard F. Love, Fishkill, both of N.Y.

[73] Assignee: Texaco Inc., New York, N.Y.

[22] Filed: June 23, 1975

[21] Appl. No.: 589,327

[52] U.S. Cl. .............................. 260/413; 260/540; 260/541; 260/597 R; 260/644

[51] Int. Cl.$^2$ .................. C07C 51/00; C07C 53/00; C07C 53/08; C07C 53/22

[58] Field of Search ............... 260/413, 526 R, 540, 260/593 R, 644 R, 541

[56] References Cited

UNITED STATES PATENTS 3,518,302   6/1970   Ellis .................................... 260/413

*Primary Examiner*—Winston A. Douglas
*Assistant Examiner*—P. E. Konopka
*Attorney, Agent, or Firm*—T. H. Whaley; C. G. Ries; George J. Darsa

[57] ABSTRACT

A method of preparing carboxylic acids is provided by contacting an ammonium, Group IA or Group IIA metal salt of a nitroketone in an aqueous medium. The method is preferably undertaken in the presence of an acidic mineral acid salt.

12 Claims, No Drawings

PREPARATION OF CARBOXYLIC ACIDS FROM SALTS OF NITROKETONES

BACKGROUND OF THE INVENTION

This invention relates to a novel method of preparing carboxylic acids and particularly to the preparation of carboxylic acids from salts of nitroketones.

Nitroketones can be converted to carboxylic acids by contacting with aqueous sodium hydroxide or refluxing in sodium acetate. The method requires isolation of the intermediate and acidification to convert the intermediate sodium carboxylate to the acid. In another method involving the refluxing of nitroketones in aqueous ammonium hydroxide, there resulted a mixture of carboxylic acids and amides. U.S. Pat. No. 3,415,856 describes a method of preparing carboxylic acids by contacting the nitroketone with water in the presence of an acid such as a mineral acid, a hydrocarbon sulfonic acid or a haloacetic acid, and where the method produces two distinct carboxylic acids. While yields of 60 and 70 mole percent of monocarboxylic acids are indicated as provided by the method, there still remains substantial room for improvement. We have now found a method whereby carboxylic acids can be produced in yields as high as 90 percent and greater, which method also provides as a valuable coproduct a nitroalkane.

It is, therefore, an object of this invention to provide a method for the preparation of carboxylic acids in high yields.

Another object of this invention is to provide a method for the preparation of carboxylic acids from salts of nitroketones in the absence of forming substantial amounts of by-products such as amides.

Yet, another object of this invention is to provide a method for converting a salt of a nitroketone to a carboxylic acid and a nitroalkane.

Othe objects and advantages will become apparent from a reading of the following detailed description and examples.

SUMMARY OF THE INVENTION

Broadly, this invention contemplates a method of preparing a carboxylic acid which comprises contacting an ammonium, Group IA or Group IIA metal salt of a nitroketone in an aqueous medium. In a preferred embodiment of this invention, the contacting is undertaken in the presence of an acidic mineral acid salt.

Pursuant to this invention, the salt of the nitroketone converted to the carboxylic acid corresponds to the formula:

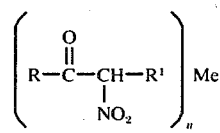

where R is an alkyl group of from 1 to 25 carbon atoms and preferably from 1 to 20 carbon atoms, where $R^1$ is hydrogen or an alkyl group having from 1 to 25 carbon atoms and preferably from 1 to 20 carbon atoms, where Me is $NH_4$, a Group IA metal or a Group IIA metal and where $n$ is 1 to 2. Illustrative of the Group IA metals are lithium, sodium and potassium and the Group IIA metals are represented by magnesium, calcium, strontium and barium. The preferred nitroketone salts are those of ammonium, sodium, calcium and magnesium. The highly preferred salt is that of ammonium. As can be seen, the contemplated salts include both terminal and internal nitroketones as each undergoes the conversion to the desired carboxylic acid along with the formation of a nitroalkane.

The method contemplated by this invention can be seen by the following equation:

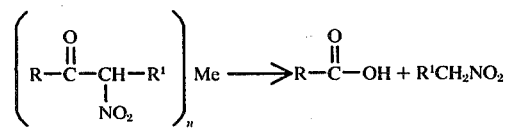

where R, $R^1$, $n$ and Me are heretofore defined. From the equation it will be seen that the reaction involves cleavage and hydrolysis of the salt to provide the alkanoic acid and the nitroalkane. When Me is ammonium in the equation above, ammonia is formed by the method. When Me is a Group IA or IIA metal, carboxylic acid and metal carboxylate are formed.

Examples of suitable nitroketone salts employed as starting material in the method of this invention include for purposes of illustration ammonium 1-nitro-2-butanone, ammonium 2-nitro-3-butanone, ammonium 1-nitro-2-pentanone, ammonium 2-nitro-3-pentanone, ammonium 1-nitro-2-hexanone, ammonium 5-nitro-4-octanone, ammonium 4-nitro-5-decanone, ammonium 5-nitro-4-dodecanone, ammonium 1-nitro-2-hexadecanone, ammonium 8-nitro-7-heptadecanone and ammonium 3-nitro-4-eicosanone. Mixture of ammonium salts of nitroketones can also be employed and provide as product mixtures of carboxylic acids and nitroalkanes. The corresponding Group IA and IIA metal salts are also contemplated and illustrated by sodium 1-nitro-2-butanone, potassium 3-nitro-4-hexanone, lithium 2-nitro-3-pentanone, magnesium 5-nitro-4-octanone, calcium 1-nitro-2-decanone, barium 1-nitro-2-decanone, strontium 5-nitro-4-dodecanone as well as mixtures of Groups IA or IIA salts of the nitroketones. The half salts of the Group IIA metals are also contemplated by this method.

As representatives of the acids prepared by the instant method, we mention the following carboxylic acids: acetic acid, propanoic acid, n-butanoic acid, n-pentanoic acid, n-hexanoic acid, 4-methylhexanoic acid, 3,3-dimethylpentanoic acid, n-heptanoic acid, n-octanoic acid, n-decanoic acid, n-dodecanoic acid, n-tetradecanoic acid, n-pentadecanoic acid and n-eicosanoic acid. Nitroalkanes prepared by the method include, for example nitromethane, nitroethane, nitropropane, nitrobutane, nitrooctane and nitrododecane.

The salts of the nitroketones employed as starting materials above can be prepared from an alkene corresponding to the formula:

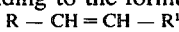

where R, $R^1$ are as heretofore defined, by contacting the alkene with dinitrogen tetroxide and oxygen at a temperature between about $-40°$ and $20°$ C. employing a mole ratio of alkene to dinitrogen tetroxide to oxygen of between about 1:1:1 and 1:1.5:30, to form a nitroperoxy intermediate of the formula:

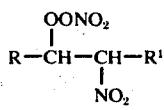

Thereafter the peroxy compound is contacted with a denitrating agent of the type known to the art at a temperature of between about −60° and 70° C. employing a mole ratio of denitrating agent to peroxy compound of about 1:1 to about 20:1 to form a nitroketone of the formula:

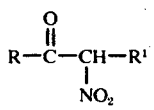

Alternatively, the alkene can be simultaneously contacted with dinitrogen tetroxide, oxygen and denitrating agent at a temperature of about 0° to 40° C. to directly prepare the above nitroketone. Representative denitrating agents include dimethylformamide, diethylformamide, dimethylacetamide, dimethylsulfoxide, diethylsulfoxide, tetramethylurea, tetraethylurea, hexamethylenephosphoramide, 1-methyl-2-pyrrolidinone, and 1,3-dimethyl-2-pyrrolidinone. The reaction is generally conducted under conditions of agitation and in the presence of an inert liquid diluent, such as n-hexane, n-heptane, carbontetrachloride or benzene. The nitroketone can, if desired, be recovered by standard recovery procedures as for example, by filtration of the solids after the addition of the reaction mixture to water or by distillation. The nitroketone is converted to the ammonium, Group IA metal or Group IIA metal salt by contacting with about 1 to 10, preferably about 1 to 1.1 moles of ammonia, a Group IA metal hydroxide or a Group IIA metal oxide or hydroxide per mole of nitroketone of a temperature of about −10° to 30° C.

In another embodiment, the reaction mixture above containing the nitroketone is contacted with about 2 to 10, preferably about 2 to 2.1 moles of ammonia, Group IA metal hydroxide or Group IIA metal hydroxide or oxide, thereby converting the nitroketone to the corresponding ammonium, Group IA or Group IIA metal salt. The salts, so formed, are insoluble in the product formed from the aforementioned nitrooxidation and denitration reactions and are easily separated therefrom employing any well-known technique as for example, filtration, centrifugation or decantation.

The salt of the nitroketone is contacted with water at a temperature of about 20° to 100° C., preferably about 90° to 100° C. whereby the salt is transformed to the carboxylic acid through conversion and cleavage and a nitroalkane is formed as a by-product. Generally, from 10 to 100 parts by weight of water per part of nitroketone salt can be employed. In the course of transforming the salt of the nitroketone in the aqueous medium to the corresponding carboxylic acid or salt, the reaction may be accompanied by foaming. It has been found that conducting the reaction in the presence of an acidic mineral acid salt permits the reaction to take place in the absence of foam. As acidic mineral acid salts contemplated herein, we include for example ammonium chloride, ammonium nitrate, ammonium sulfate, ammonium hydrogen sulfate, ammonium phosphate or calcium nitrate. Highly preferred acidic mineral acid salts employed in the course of the reaction are ammonium nitrate or calcium nitrate. The mole ratio of nitroketone salt to acidic mineral acid salt employed herein can range from about 1:0.01 to 1:2 and preferably from about 1:0.5 to 1:1.5. At the completion of the conversion and cleavage reaction, a hydrocarbon solvent can be added to the reaction mixture as an aid in separating out the nitroalkane. Appropriate hydrocarbon solvents include $C_6$ to $C_9$ aromatics, such as benzene, toluene, xylenes and trimethylbenzenes; $C_6$ to $C_{12}$ alkanes, such as hexane, heptane, decane and dodecane; and $C_6$ to $C_{12}$ cycloalkane, such as cyclohexane, methylcyclohexane, dimethylcyclohexane, cyclooctane and cyclododecane. Further, when the ammonium salt of the nitroketone is employed as the starting material, distillation to remove the nitroalkane also separates out ammonia. When a Group IA or a Group IIA metal salt of a nitroketone is employed the metal component is separated as the metal salt of the carboxylic acid and the carboxylic acid is recovered by acidification with dilute mineral acid. When the ammonium salt of the nitroketone is used in conjunction with an acid salt such as ammonium nitrate, no acidication with a mineral acid is required as the carboxylic acid may be obtained directly from the reaction mixture.

By the instant method, the salts of the nitroketones can be selectively converted to carboxylic acids in yields as high as 95 percent. The acids prepared according to this invention are useful as chemical intermediates for the preparation of detergents, emulsifiers, turbine oils, plasticizers, paints, anti-freezing agents and rubbers.

In order to more fully illustrate the nature of this invention and the manner of practicing the same the following examples are presented.

EXAMPLE I

Into a 300 milliliter flask equipped with a gas inlet, thermometer and condenser, there was charged 22.6 grams (0.1 mole) of 1-hexadecene and 100 milliliters of carbon tetrachloride. To this solution, maintained at a temperature of 10° C., there was introduced oxygen at the rate of 100 milliliters per minute and 9.2 grams (0.1 mole) of dinitrogen tetroxide at the rate of 0.05 gram per minute over a period of 3 hours. At the end of the dinitrogen tetroxide-oxygen addition period, 11 grams (0.15 mole) of dimethylformamide as denitrating agent were added over a period of one-quater hour while maintaining the temperature at 10° C.

To the above crude composition maintained at 10° C., there was introduced 3.4 grams (0.2 mole) of ammonia as a gas at the rate of 0.11 gram per minute over a period of one-half hour. The solids composed of ammonium nitrate and the ammonium salt of 1-nitro-2-hexadecanone were separated from the crude composition by filtration and weighed 36 grams. The ammonium salt of the nitroketone (28 grams) and ammonium nitrate (8 grams) were charged into a 500 milliliter flask equipped with a thermometer and condenser. 300 milliliters of water were added and the reaction mixture was refluxed at 100° C. for three hours. Thereafter, 200 milliliters of benzene were added and azeotropic distillation of the benzene removed 5.7 grams of nitromethane corresponding to a yield of 95 percent. The reaction mixtire was filtered and 23.0 grams of petadecanoic acid corresponding to a yield of 95 percent was recovered.

EXAMPLE II

Tetradecene (19.8 grams, 0.1 mole) and dimethylformamide (20 milliliters, 0.26 mole) dissolved in 100 milliliters of benzene were treated with a 1:6 volume to volume ratio mixture of dinitrogen tetroxide (9.2 grams, 0.1 mole) and oxygen at 10° C. over a period of four hours and the mixture was swept with oxygen for an addition 15 minutes. Calcium oxide (5.6 grams, 0.1 mole) was added to the cooled stirred mixture and after 30 minutes, the solid material (37.6 grams) was separated by filtration and 300 milliliters of water were added thereto. After one hour at reflux, the solution was cooled and acidified with 6N hydrochloric acid to precipitate 19.8 grams (92 percent yield) of tridecanoic acid.

EXAMPLE III

The ammonium salt of 1-nitro-2-hexadecanone (27 grams, 0.098 mole) mixed with 300 milliliters of water was refluxed in a 500 milliliter flask using a knock back condenser. After a few minutes at reflux, considerable foaming occured lifting the liquids and solids out the top of the condenser. By introducing ammonium nitrate (approximately 5 grams), the foaming was reduced and controlled.

EXAMPLE IV

A mixture of ammonium nitrate (4.0 grams, 0.05 mole), 1-nitro-2-hexadecanone (12.8 grams, 0.05 mole) and 200 milliliters of water were refluxed at 101° C. for 2 hours. Upon cooling 12.5 grams of solids were recovered by filtration. Analysis by nuclear magnetic resonance of this material indicated that it was 95 percent 1-nitro-2-hexadecanone.

EXAMPLE V 1-nitro-2-octadecanone (1.0 gram, 3.2 mmoles) was added to 20 milliliters of concentrated (28 percent) aqueous ammonium hydroxide and the mixture refluxed for four hours. After cooling and diluting with 100 milliliters of water, 0.77 gram (89 percent yield) of heptadecanamide was obtained. The aqueous solution was evaporated to dryness and 0.3 gram of a mixture of heptadecanoic acid and its ammonium salt were obtained. No nitromethane was detected.

EXAMPLE VI

Into a 300 milliliter flask equipped with a gas inlet, thermometer and condenser, there was charged 24.0 grams (0.1 mole) of 7-heptadecene and 100 milliliters of carbon tetrachloride. To this solution maintained at 10° C., there was introduced oxygen at the rate of 100 milliliters per minute and 9.2 grams (0.1 ) of dinitrogen tetroxide at the rate of 0.05 gram per minute over a period of 3 hours. At the end of the dinitrogen tetroxide-oxygen addition period, 11 grams (0.15 mole) of dimethylformamide were added over a period of one-quarter hour while maintaining the temperature at 10° C.

To the crude composition maintained at 10° C. there was introduced 5.6 grams (0.1 mole) of calcium oxide. After stirring for 30 minutes, the solids composed of calcium nitrate and the calcium salt of the nitroketone were separated by filtration and weighed 38.0 grams.

The solids were then charged to a 500 milliliters flask and refluxed with 300 milliliters of water for three hours. Extraction of the reaction mixture with three 100 milliliter portions of ethylether afforded after drying and stripping 16.0 grams of a mixture of nitroheptane and nitrodecane (92 percent yield). The water layer was acidified with 6N hydrochloric acid thereby precipitating 14.8 grams of a mixture of decanoic and heptanoic acids (92 percent yield).

EXAMPLE VII

The procedure of Example VI was repeated except 11.0 grams (0.1 mole) of 4-octene was employed as starting material and 27.0 grams of solids composed of calcium nitrate and the calcium salt of the nitroketone were separated by filtration. Extraction and acidification provided 8.7 grams of nitrobutane (92 percent yield) and 7.9 grams of butanoic acid (90 percent yield).

We claim:

1. A method of preparing a carboxylic acid which comprises contacting an ammonium, Group IA or Group IIA metal salt of a nitroketone corresponding to the formula:

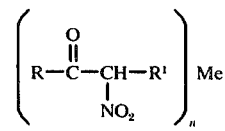

where R is an alkyl group of from 1 to 25 carbon atoms, where $R^1$ is hydrogen or an alkyl group of from 1 to 25 carbon atoms, where Me is $NH_4$, a Group IA metal or a Group IIA metal and where $n$ is 1 to 2, at a temperature of about 20° to 100° C. with from 10 to 100 parts by weight of water per part by weight of said nitroketone salt in the presence of an acidic mineral acid salt, wherein said acidic salt is ammonium chloride, ammonium nitrate, ammonium sulfate, ammonium hydrogen sulfate, ammonium phosphate or calcium nitrate, where the mole ratio of said nitroketone salt to said acidic salt is from about 1:0.01 to 1:2.

2. A method according to claim 1 wherein said contacting is at a temperature of about 90° to 100° C.

3. A method according to claim 1 wherein said nitroketone salt is ammonium 1-nitro-2-hexadecanone.

4. A method according to claim 1 wherein said nitroketone salt is ammonium 7-nitro-8-heptadecanone.

5. A method according to claim 1 wherein said nitroketone salt is ammonium 5-nitro-4-octanone.

6. A method according to claim 1 wherein said nitroketone salt is calcium 1-nitro-2-hexadecanone.

7. A method according to claim 1 wherein said nitroketone salt is calcium 5-nitro-4-octanone.

8. A method according to claim 1 wherein said acid salt is ammonium nitrate.

9. A method according to claim 1 wherein said acid salt is ammonium sulfate.

10. A method according to claim 1 wherein said acid salt is ammonium chloride.

11. A method according to claim 1 wherein said acid salt is ammonium phosphate.

12. A method according to claim 1 wherein said acid salt is calcium nitrate.

* * * * *